United States Patent [19]
Pauza

[11] Patent Number: 6,027,731
[45] Date of Patent: Feb. 22, 2000

[54] PERTUSSIS TOXIN INDUCED LYMPHOCYTOSIS

[75] Inventor: C. David Pauza, Madison, Wis.

[73] Assignee: Wisconsin Alumni Research Foundation, Madison, Wis.

[21] Appl. No.: 09/193,654

[22] Filed: Nov. 17, 1998

Related U.S. Application Data

[60] Division of application No. 08/793,655, filed as application No. PCT/US95/11004, Aug. 29, 1995, Pat. No. 5,888,726, which is a continuation-in-part of application No. 08/299,890, Sep. 1, 1994, abandoned.

[51] Int. Cl.$^7$ ..................................................... A01N 37/18
[52] U.S. Cl. ..................................... 424/240.1; 424/184.1; 424/234.1; 424/236.1; 424/278.1; 424/282.1
[58] Field of Search ............................... 424/184.1, 234.1, 424/236.1, 240.1, 278.1, 282.1

[56] References Cited

U.S. PATENT DOCUMENTS

| | | | |
|---|---|---|---|
| 5,173,399 | 12/1992 | Mehta et al. | 435/5 |
| 5,667,964 | 9/1997 | Ho | 435/5 |

FOREIGN PATENT DOCUMENTS

| | | |
|---|---|---|
| 0471177 | 2/1992 | European Pat. Off. . |
| WO8804665 | 6/1988 | WIPO . |
| WO9101143 | 2/1991 | WIPO . |
| WO9116926 | 11/1991 | WIPO . |
| WO9202243 | 2/1992 | WIPO . |
| WO9219269 | 11/1992 | WIPO . |

OTHER PUBLICATIONS

Person et al., "Pertussis Toxin–Induced Lymphocytosis is Associated with Alterations in Thymocyte Subpopulations," Journal of Immunology, vol. 148, No. 5 (Mar. 1, 1992), pp. 1506–1511.

Pauza et al, "SIV Transmission Across the Mucosal Barrier," AIDS Research and Human Retroviruses, vol. 10, Supp. 1, 1994, Mary Ann Liebert, Inc. Publishers.

Salvato et al, "Cellular Immune Responses in Rhesus Macaques Infected Rectally with Low Dose Simian Immunodeficiency Virus," J. Med. Primatol, 23, pp. 125–130, 1994.

Wallace, "Antiviral Activity of Primate $\beta\delta$ T Lymphocytes Isolated by Magnetic Cell Sorting," J. Med. Primatol, 23, pp. 131–135, 1994.

Pauza et al, "Pathogenesis of $SIV_{mac251}$ After Atraumatic Inoculation of the Rectal Mucosa in Rhesus Monkeys," J. Med. Primatol, 22, pp. 154–161, 1993.

Pauza, "Acquired Resistance to Mucosal SIV Infection After Low Dose Intrarectal Inoculation: The Roles of Virus Selection and CD8–Mediated T Cell Immunity," Huitieme Colloque Des Cent Gardes, pp. 151–156, 1993.

Pauza, "Transmission of SIV by Intrarectal Inoculation in Rhesus Monkeys," Septieme Colloque Des Cent Gardes, pp. 69–74, 1992.

Trivedi et al, "Selective Amplification of Simian Immunodeficiency Virus Genotypes After Intrarectal Inoculation of Rhesus Monkeys," Journal of Virology, vol. 68, No. 11, pp. 7649–7653, Nov., 1994.

*Primary Examiner*—Jeffrey Stucker
*Attorney, Agent, or Firm*—Andrus, Sceales, Starke & Sawall

[57] ABSTRACT

A therapeutic remodeling of immune system for HIV evaluation and AIDS treatment. Specifically, the present invention involves eliciting lymphocytosis in order to reveal the sequestered HIV or SIV in the lymph tissues enabling HIV infection analysis, viral quantification and treatment. The lymphocytosis itself causes an alleviation of the AIDS symptoms and a reduction in the viral load. The present invention could also be used in conjunction with a large variety of adjunct therapies.

12 Claims, 18 Drawing Sheets

| Date: | DAY: | WBC: | RBC: (E7) | %Seg | %Bnd | %lym | %mon | %Eos | %Baso | Abs. Seg |
|---|---|---|---|---|---|---|---|---|---|---|
| | | | PERTUSSIS TOXIN EFFECTS: | | | | | | | |
| | | | R90141 - Normal 25ug dose | | | | | | | |
| 27-Jan | 0 | 10,800 | 6.58 | 46 | 3 | 49 | 2 | 0 | 0 | 4968 |
| 31-Jan | 3 | 9,800 | 5.7 | 25 | 0 | 68 | 6 | 1 | 0 | 2450 |
| 3-Feb | 7 | 13,600 | 6.14 | 28.5 | 1.5 | 65 | 3 | 2 | 0 | 3876 |
| | | | R90128 - Normal 50ug dose | | | | | | | |
| 27-Jan | 0 | 12,000 | 5.12 | 57 | 0 | 39 | 2 | 2 | 0 | 6840 |
| 31-Jan | 3 | 13,500 | 5.21 | 11 | 0 | 85 | 4 | 0 | 0 | 1485 |
| 3-Feb | 7 | 13,300 | 5.06 | 18 | 0 | 79 | 3 | 0 | 0 | 2394 |
| | | | R90144 - Normal 100ug dose | | | | | | | |
| 27-Jan | 0 | 17,100 | 5.13 | 23 | 1 | 71 | 2 | 3 | 0 | 3933 |
| 31-Jan | 3 | 64,500 | 5.08 | 16 | 4 | 76 | 4 | 0 | 0 | 10320 |
| 3-Feb | 7 | 54,400 | 4.95 | 16 | 4 | 74 | 4 | 2 | 0 | 8704 |
| 10-Feb | 14 | 33,600 | 5.3 | 20.5 | 7 | 68.5 | 3.5 | 0.5 | 0 | 6888 |

KEY:

DAY (days after PTx administration)

WBC (white blood cell count in cells per µl blood)

RBC (red blood cell count)

% seg (frequency of segmented cells that are probably polymorphonuclear lymphocytes)

% bnd (banded cells that are part of the myeloid differentiation series)

% lym (lymphocyte population)

% mon (monocyte/macrophage population)

% Eos (eosinophils)

% Baso (basophils)

FIG. 1

Laboratory Data for 3rd Normal Group (older): PT treated.
PT Treatment: Monday 1 Aug 94 {100µg IV}
SIV Infection: (uninfected as of 4 Aug 94)

R87012   Male   (Saline Control)

| Day: | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|---|
| 0 | 10900 | 0 | 5.51 | 46 | 1 | 44 | 5 | 4 | 0 | 5014 | 4796 | 545 | 109 |
| 1 | 7900 | -27.5 | 5.47 | 56.8 | 0 | 35.6 | 7.6 | 0 | 0 | 4487.2 | 2812.4 | 600.4 | 0 |
| 4 | 9400 | -13.8 | 5.27 | 37.6 | 0 | 52.5 | 3.3 | 6.4 | 0.2 | 3534.4 | 4935 | 310.2 | 0 |
| 8 | 7400 | -32.1 | 5.39 | 50 | 0 | 44 | 2 | 4 | 0 | 3700 | 3256 | 148 | 0 |
| 16 |   | -100 |   |   |   |   |   |   |   |   | 0 | 0 | 0 |
| 32 |   | -100 |   |   |   |   |   |   |   |   | 0 | 0 | 0 |

R87012

| Day: | Glucose | BUN | Creat | Chol | Trig | SGOT | LDH | T.B. | SGPT | T.P. | Alb. | Alk PO4 |
|---|---|---|---|---|---|---|---|---|---|---|---|---|
| 0 | 78 | 18 | 1.2 | 159 | 58 | 22 | 246 | 0.1 | 15 | 7.2 | 4.5 | 120 |
| 1 |   |   |   |   |   |   |   |   |   |   |   |   |
| 4 |   |   |   |   |   |   |   |   |   |   |   |   |
| 8 | 64 | 12 | 1.2 | 156 | 28 | 30 | 528 | 0.2 | 19 | 6.9 | 4.1 | 124 |
| 16 |   |   |   |   |   |   |   |   |   |   |   |   |
| 32 |   |   |   |   |   |   |   |   |   |   |   |   |

FIG. 2A

R87031 Male

| Day: | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|
| 0 | 7700 | 0 | 6.25 | 56.6 | 0 | 36.5 | 3.3 | 3.3 | 0.3 | 4358.2 | 2810.5 | 254.1 | 0 |
| 1 | 22600 | 193.5 | 6.45 | 60.6 | 0 | 30.7 | 8.7 | 0 | 0 | 13695.6 | 6938.2 | 1966.2 | 0 |
| 2 | 45400 | 489.6 | 6.16 | 60.5 | 14 | 19 | 6 | 0.5 | 0 | 27467 | 8626 | 2724 | 6356 |
| 4 | 70100 | 810.4 | 6.08 | 68 | 14 | 13 | 4 | 1 | 0 | 47668 | 9113 | 2804 | 9814 |
| 7 | 72600 | 842.9 | 6.15 | 63 | 3 | 32 | 1 | 1 | 0 | 45738 | 23232 | 726 | 2178 |
| 8 | 27600 | 258.4 | 5.55 | 49 | 2 | 43 | 6 | 0 | 0 | 13524 | 11868 | 1656 | 552 |
| 10 | 55400 | 619.5 | 6.12 | 36 | 15.5 | 48 | 0.5 | 0 | 0 | 19944 | 26592 | 277 | 8587 |
|  |  | −100 |  |  |  |  |  |  |  | 0 | 0 | 0 | 0 |

R87031

| Day: | Glucose | BUN | Creat | Chol | Trig | SGOT | LDH | T.B. | SGPT | T.P. | Alb. | Alk PO4 |
|---|---|---|---|---|---|---|---|---|---|---|---|---|
| 0 | 70 | 15 | 1.3 | 155 | 88 | 43 | 579 | 0.2 | 32 | 7.6 | 4.2 | 155 |
| 1 |  |  |  |  |  |  |  |  |  |  |  |  |
| 2 | 66 | 14 | 1.2 | 110 | 44 | 84 | 347 | 0.1 | 108 | 6.7 | 3.6 | 152 |
| 4 | 91 | 19 | 1.4 | 106 | 98 | 56 | 388 | 0.2 | 123 | 7.2 | 3.2 | 252 |
| 7 | 65 | 95 | 3 | 173 | 493 | 282 | 1095 | 0.2 | 162 | 5.9 | 2.1 | 347 |
| 8 | 95 | 65 | 1.4 | 169 | 330 | 448 | 2085 | 0.2 | 360 | 6 | 2.3 | 263 |
| 10 |  |  |  |  |  |  |  |  |  |  |  |  |

FIG. 2B

R88028 (Female)

| Days Post | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|---|
| 0 | 7100 | 0 | 5.76 | 34 | 0 | 63 | 2 | 1 | 0 | 2414 | 4473 | 142 | 0 |
| 1 | 9000 | 26.76 | 5.79 | 43.1 | 0 | 44.2 | 12.7 | 0 | 0 | 3879 | 3978 | 1143 | 0 |
| 2 | 11100 | 56.34 | 5.52 | 15 | 0 | 77 | 5 | 3 | 0 | 1665 | 8547 | 555 | 0 |
| 4 | 24300 | 242.3 | 5.52 | 12 | 6 | 79 | 2 | 0 | 0 | 2916 | 19197 | 486 | 1458 |
| 8 | 19000 | 167.6 | 5.64 | 18 | 3 | 75 | 3 | 1 | 0 | 3420 | 14250 | 570 | 570 |
| 16 | | -100 | | | | | | | | 0 | 0 | 0 | 0 |
| 32 | | -100 | | | | | | | | 0 | 0 | 0 | 0 |

R88028

| Days Post | Glucose | BUN | Creat | Chol | Trig | SGOT | LDH | T.B. | SGPT | T.P. | Alb. | Alk PO4 |
|---|---|---|---|---|---|---|---|---|---|---|---|---|
| 0 | 58 | 10 | 0.8 | 127 | 61 | 27 | 290 | 0.2 | 21 | 6.9 | 4.6 | 191 |
| 1 | | | | | | | | | | | | |
| 2 | 68 | 8 | 0.8 | 115 | 26 | 46 | 567 | 0.2 | 35 | 6.8 | 4.4 | 209 |
| 4 | 71 | 10 | 0.8 | 118 | 26 | 62 | 516 | 0.2 | 46 | 6.6 | 4.1 | 196 |
| 8 | 56 | 9 | 0.8 | 128 | 33 | 64 | 980 | 0.2 | 46 | 6.6 | 4.2 | 201 |
| 16 | | | | | | | | | | | | |
| 31 | | | | | | | | | | | | |

R88040 (Female)

| Days Post | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|---|
| 0 | 7900 | 0 | 6.32 | 39.8 | 1 | 52.8 | 1.9 | 4.2 | 1.3 | 3144.2 | 4171.2 | 150.1 | 79 |
| 1 | 15100 | 91.14 | 6.51 | 46.5 | 0 | 47.5 | 6 | 0 | 0 | 7021.5 | 7172.5 | 906 | 0 |
| 2 | 30400 | 284.8 | 6.47 | 50 | 6 | 32 | 9 | 3 | 0 | 15200 | 9728 | 2736 | 1824 |
| 4 | 32700 | 313.9 | 5.4 | 50 | 2 | 42 | 4 | 1 | 1 | 16350 | 13734 | 1308 | 654 |
| 8 | 53000 | 570.9 | 5.08 | 33 | 13 | 48 | 5 | 1 | 0 | 17490 | 25440 | 2650 | 6890 |
| 16 | | −100 | | | | | | | | 0 | 0 | 0 | 0 |
| 32 | | −100 | | | | | | | | 0 | 0 | 0 | 0 |

R88040

| Days Post | Glucose | BUN | Creat | Chol | Trig | SGOT | LDH | T.B. | SGPT | T.P. | Alb. | Alk PO4 |
|---|---|---|---|---|---|---|---|---|---|---|---|---|
| 0 | 102 | 15 | 0.7 | 190 | 53 | 36 | 526 | 0.2 | 21 | 7.3 | 4.3 | 245 |
| 1 | 88 | 12 | 0.8 | 154 | 63 | 94 | 631 | 0.3 | 48 | 7.1 | 4.1 | 243 |
| 2 | 67 | 19 | 0.7 | 124 | 51 | 138 | 770 | 0.4 | 105 | 7 | 3.9 | 231 |
| 4 | 75 | 19 | 0.9 | 99 | 51 | 70 | 800 | 0.3 | 136 | 6.4 | 3.2 | 177 |
| 8 | 66 | 12 | 0.5 | 138 | 137 | 92 | 1536 | 0.1 | 81 | 5.9 | 2.7 | 243 |
| 16 | | | | | | | | | | | | |
| 32 | | | | | | | | | | | | |

FIG. 2D

|         | CD2  | CD4   | CD8   | CD20  | CD4/CD8 |
|---------|------|-------|-------|-------|---------|
| 90065pre | 49.6 | 11.98 | 46.5  | 11.44 | 0.26    |
| post    | 74.8 | 29.5  | 31.6  | 10.9  | 0.93    |
| leukocytosis => 3.5X | | | | | |
| 90087pre | **   | 31.2  | 25.3  | 1.9   | 11.2    |
| 3 d post | 74.2 | 43.2  | 36.3  | 10.8  | 1.2     |
| 45 d post | 89.7 | 21.1 | 49.42 | **    | 0.5     |
| leukocytosis => maybe 2 | | | | | |
| 90112pre | 45.6 | 21.5  | 21    | 15.5  | 1       |
| 3 d post | 67   | 38.3  | **    | 4.3   | **      |
| 45 d post | 86  | 20    | 59    | 1.3   | 0.3     |
| leukocytosis => 3.2X | | | | | |

FIG. 4A

90047 SIV hemo

| | 1 | 2 | 3 | 4 | 5 | 6 | 7 | 8 | 9 | 10 | 11 | 12 | 13 |
|---|---|---|---|---|---|---|---|---|---|---|---|---|---|
| | date | wbc | rbc | abs PMN | abs Lymphs | abs Mono | abs Bands | %Segs | %Bands | %Lymphs | %Monos | %Eos | %Baso |
| 1 | (7) | 7500 | 4.28 | 3150 | 3075 | 675 | 0 | 42 | 0 | 41 | 9 | 7 | 1 |
| 2 | 0 | 7500 | 4.37 | 2550 | 3600 | 900 | 75 | 34 | 1 | 48 | 12 | 5 | 0 |
| 3 | 3 | 65100 | 5.21 | 31248 | 23436 | 5859 | 4557 | 48 | 7 | 36 | 9 | 0 | 0 |
| 4 | 7 | 43200 | 5.47 | 18144 | 18576 | 3888 | 2592 | 42 | 6 | 43 | 9 | 0 | 0 |
| 5 | 14 | 22900 | 5.12 | 11221 | 9618 | 687 | 687 | 49 | 3 | 42 | 3 | 3 | 0 |
| 6 | 21 | 14100 | 5.01 | 7755 | 4794 | 705 | 846 | 55 | 6 | 34 | 5 | 0 | 0 |
| 7 | 28 | 11000 | 5.08 | 6930 | 2530 | 440 | 550 | 63 | 5 | 23 | 4 | 5 | 0 |
| 8 | 42 | 9600 | 3.88 | 4995 | 3456 | 768 | 192 | 52 | 2 | 36 | 8 | 2 | 0 |
| 9 | 63 | 6900 | 5.10 | 2346 | 3036 | 759 | 0 | 34 | 0 | 44 | 11 | 10 | 1 |
| 10 | 75 | 8500 | 4.85 | 3995 | 3400 | 680 | 0 | 47 | 0 | 40 | 8 | 5 | 0 |
| 11 | 87 | 9300 | 5.31 | 4836 | 3720 | 744 | 0 | 52 | 0 | 40 | 8 | 0 | 0 |
| 12 | 95 | 10800 | 4.98 | 7236 | 2268 | 972 | 108 | 67 | 1 | 21 | 9 | 2 | 0 |
| 13 | 122 | 6100 | 4.19 | 3842 | 1586 | 427 | 122 | 63 | 2 | 26 | 7 | 2 | 0 |

FIG. 4B 90019 hemo data

| | 1 | 2 | 3 | 4 | 5 | 6 | 7 | 8 | 9 | 10 | 11 | 12 | 13 |
|---|---|---|---|---|---|---|---|---|---|---|---|---|---|
| | date | wbc | rbc | abs PMN | abs Lymphs | abs Mono | abs Bands | %PMN | %Bands /meta | %Lymphs | %Monos | %Eos | %Baso |
| 1 | -14 | 9000 | 5.48 | 3150 | 4570 | 260 | 0 | 44.2 | 0 | 40.9 | 2.9 | 1.6 | 0.4 |
| 2 | 0 | 7900 | 5.51 | 3600 | 3900 | 270 | 0 | 45.3 | 0 | 49.2 | 3.4 | 1.8 | 0.3 |
| 3 | 3 | 52400 | 5.41 | 15750 | 31440 | 3144 | 1572 | 30 | 3 | 60 | 6 | 1 | 0 |
| 4 | 15 | 26600 | 5.44 | 2394 | 23674 | 266 | 266 | 9 | 1 | 89 | 1 | 0 | 0 |
| 5 | 27 | 11500 | 5.59 | 1208 | 9832 | 288 | 0 | 10.5 | 0 | 85.5 | 2.5 | 1 | 0.5 |
| 6 | 31 | 13900 | 5.37 | 2919 | 9869 | 834 | 0 | 21 | 0 | 71 | 6 | 2 | 0 |
| 7 | 41 | 9500 | 5.25 | 3515 | 4845 | 760 | 95 | 37 | 1 | 51 | 8 | 1 | 2 |
| 8 | 62 | 8100 | 5.49 | 4110 | 3610 | 300 | 0 | 50.5 | 0 | 44.3 | 3.7 | 1.3 | 0.2 |
| 9 | | | | | | | | | | | | | |
| 10 | | | | | | | | | | | | | |
| 11 | | | | | | | | | | | | | |
| 12 | | | | | | | | | | | | | |
| 13 | | | | | | | | | | | | | |

Leukocytosis in PTx Treated (100 μg i.v.) Animals Infected (3 years intrarectal)

| | PBMC req'd for positive | Corr. CD4 Number | tissue/blood virus load |
|---|---|---|---|
| 90019pre | 10,000 | 2500 | |
| 8 d. post | 1,000 | 250 | 100 |
| d 14 to 84 | >1,000,000 | | |
| 84 d. | 1,000,000 | | |
| d 84 to 143 | >1,000,000 | | |
| 154 d. | 1,000,000 | | |
| | leukocytosis => 10X | | |
| 90047pre | 100,000 | 8000 | |
| 8 d. post | 10 or 100 | 2 or 20 | 36,000 or 3,600 |
| d 14 to 28 | >1,000,000 | | |
| 28 d. | 1,000,000 | | |
| d 28 to 84 | >1,000,000 | | |
| | leukocytosis => 9 X | | |

Laboratory Data for Re-Challenge Rhesus SIV + Group: PT Treated.
PT Treatment: Monday 27 June 94 (100µg IV)
SIV Infection:
R90054

| Day: | WBC | %Inc. | RBC | %Segs | %Bands | %Lymphs | wbc | %Eos | %baso | Abs Segs | Abs Lymphs | Abs Monos | Abs bands |
|---|---|---|---|---|---|---|---|---|---|---|---|---|---|
| -27 | 4800 | -28.4 | 4.95 | 29 | 0 | 62 | 8 | 1 | 0 | 1392 | 2976 | 384 | 0 |
| 0 | 6700 | 0 | 4.66 | 52 | 1 | 32 | 10 | 5 | 0 | 3484 | 2144 | 670 | 67 |
| 1 | 38300 | 471.6 | 4.84 | 27 | 60 | 66 | 6 | 1 | 0 | 10341 | 25278 | 2298 | 22980 |
| 2 | 57800 | 762.7 | 4.68 | 28.5 | 4.5 | 62.5 | 2 | 2 | 0 | 16473 | 36125 | 1156 | 2601 |
| 3 | 64500 | 862.7 | 4.44 | 24 | 1.5 | 70.5 | 3.5 | 0.5 | 0 | 15480 | 45472.5 | 2257.5 | 967.5 |
| 8 | 85700 | 1179 | 4.15 | 35 | 22 | 38 | 2 | 2 | 0 | 29995 | 32568 | 1714 | 18854 |
| 14 | 40200 | 500 | 4.12 | 29 | 11 | 55 | 5 | 0 | 0 | 11658 | 22110 | 2010 | 4422 |

| Day: | Glucose | BUN | Creat | Chol | Trig | SGOT | LDH | T.B. | SGPT | T.P. | Alb. | Alk PO4 | Fe | Na | K | CL |
|---|---|---|---|---|---|---|---|---|---|---|---|---|---|---|---|---|
| -27 | | | | | | | | | | | | | | | | |
| 0 | 57 | 22 | 1.3 | 118 | 26 | 111 | 267 | 0.1 | 84 | 7.3 | 4 | 399 | 121 | 148 | 3.7 | 107 |
| 1 | 54 | 17 | 1.1 | 92 | 56 | 98 | 381 | 0.1 | 79 | 6.7 | 3.6 | 312 | 74 | 143 | 2.9 | 103 |
| 2 | 72 | 12 | 1 | 91 | 54 | 121 | 461 | 0.2 | 122 | 6.8 | 3.7 | 292 | 22 | 147 | 3 | 107 |
| 3 | | | | | | | | | | | | | | | | |
| 8 | 75 | 15 | 1 | 59 | 83 | 74 | 583 | 0.1 | 97 | 6.1 | 2.6 | 440 | 20 | 144 | 3.7 | 101 |
| 14 | 57 | 8 | 0.9 | 75 | 75 | 43 | 365 | 0.1 | 96 | 6.4 | 2.7 | 442 | 59 | 143 | 3.7 | 100 |

| Day: | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|---|
| -27 | 15000 | 12.78 | 5.05 | 65 | 1 | 32 | 1 | 1 | 0 | 9750 | 4300 | 150 | 150 |
| 0 | 13300 | 0 | 4.88 | 60 | 1 | 33 | 6 | 0 | 0 | 7980 | 4389 | 798 | 133 |
| 1 | 21200 | 59.4 | 5.42 | 30 | 0 | 62 | 8 | 0 | 0 | 6360 | 13144 | 1696 | 0 |
| 2 | 34300 | 157.9 | 4.99 | 36 | 12.5 | 47 | 3.5 | 1 | 0 | 12348 | 16121 | 1200.5 | 4287.5 |
| 3 | 32400 | 143.6 | 4.81 | 27 | 4 | 63 | 4 | 2 | 0 | 8748 | 20412 | 1296 | 1296 |
| 8 | 58200 | 337.6 | 4.43 | 41 | 21.5 | 30.5 | 6 | 1 | 0 | 23862 | 17751 | 3492 | 12513 |
| 14 | 30000 | 125.6 | 4.35 | 34 | 7 | 56 | 2.5 | 0.5 | 0 | 10200 | 16800 | 750 | 2100 |

| Day: | Glucose | BUN | Creat | Chol | Trig | SGOT | LDH | T.B. | SGPT | T.P. | Alb. | Alk PO4 | Fe | Na | K | CL |
|---|---|---|---|---|---|---|---|---|---|---|---|---|---|---|---|---|
| -27 | | | | | | | | | | | | | | | | |
| 0 | 52 | 19 | 1.4 | 104 | 41 | 40 | 321 | 0.1 | 53 | 7.1 | 4.4 | 428 | 198 | 150 | 4.1 | 109 |
| 1 | 64 | 17 | 1.2 | 92 | 106 | 139 | 603 | 0.3 | 123 | 6.8 | 4.2 | 375 | 142 | 151 | 4 | 112 |
| 2 | 59 | 20 | 1.1 | 83 | 72 | 118 | 677 | 0.1 | 159 | 6.7 | 4.4 | 337 | 68 | 150 | 3.4 | 110 |
| 3 | | | | | | | | | | | | | | | | |
| 8 | 36 | 22 | 1 | 63 | 162 | 70 | 1492 | 0.2 | 117 | 6.3 | 2.8 | 289 | 75 | 149 | 4.8 | 108 |
| 14 | 46 | 15 | 1 | 77 | 67 | 50 | 388 | 0.1 | 142 | 6.1 | 3 | 247 | 126 | 147 | 4 | 104 |

| Day: | WBC | %Inc. | RBC | %Segs | %Bands | %Lymphs | %Monos | %Eos | %baso | Abs Segs | Abs Lymphs | Abs Monos | Abs bands |
|---|---|---|---|---|---|---|---|---|---|---|---|---|---|
| -27 | 4800 | -4 | 5.77 | 28 | 0 | 70 | 2 | 0 | 0 | 1344 | 3360 | 96 | 0 |
| 0 | 5000 | 0 | 5.5 | 33 | 0 | 57 | 10 | 0 | 0 | 1650 | 2850 | 500 | 0 |
| 1 | 26800 | 436 | 5.52 | 43 | 0 | 50 | 6 | 1 | 0 | 11524 | 13400 | 1608 | 0 |
| 2 | 49700 | 894 | 5.67 | 36 | 5 | 56 | 1 | 2 | 0 | 17892 | 27832 | 497 | 2485 |
| 3 | 47300 | 846 | 5.26 | 33 | 3 | 60.5 | 3 | 0.5 | 0 | 15609 | 28616.5 | 1419 | 1419 |
| 8 | 42700 | 754 | 4.7 | 28.5 | 29 | 37.5 | 3.5 | 1 | 0.5 | 12169.5 | 16012.5 | 1494.5 | 12383 |
| 14 | 21000 | 320 | 5.14 | 27.5 | 0.5 | 65.5 | 6 | 0.5 | 0 | 5775 | 13755 | 1260 | 105 |

| Day: | Glucose | BUN | Creat | Chol | Trig | SGOT | LDH | T.B. | SGPT | T.P. | Alb. | Alk PO4 | Fe | Na | K | CL |
|---|---|---|---|---|---|---|---|---|---|---|---|---|---|---|---|---|
| -27 | | | | | | | | | | | | | | | | |
| 0 | 72 | 18 | 1.5 | 125 | 97 | 28 | 603 | 0.1 | 14 | 6.9 | 4.3 | 446 | 202 | 147 | 3.7 | 106 |
| 1 | 60 | 21 | 1.5 | 109 | 88 | 93 | 814 | 0.2 | 42 | 6.5 | 4.1 | 435 | 205 | 148 | 3.2 | 110 |
| 2 | 99 | 23 | 1.6 | 89 | 33 | 110 | 1022 | 0.2 | 81 | 6.4 | 4 | 402 | 21 | 149 | 2.8 | 107 |
| 3 | | | | | | | | | | | | | | | | |
| 8 | 64 | 25 | 1.2 | 79 | 246 | 62 | 1776 | 0.2 | 40 | 5.4 | 2.5 | 289 | 51 | 147 | 4.2 | 109 |
| 14 | 55 | 16 | 1.2 | 96 | 116 | 39 | 708 | 0.1 | 33 | 6.2 | 2.8 | 243 | 53 | 145 | 4.6 | 103 |

FIG. 7C

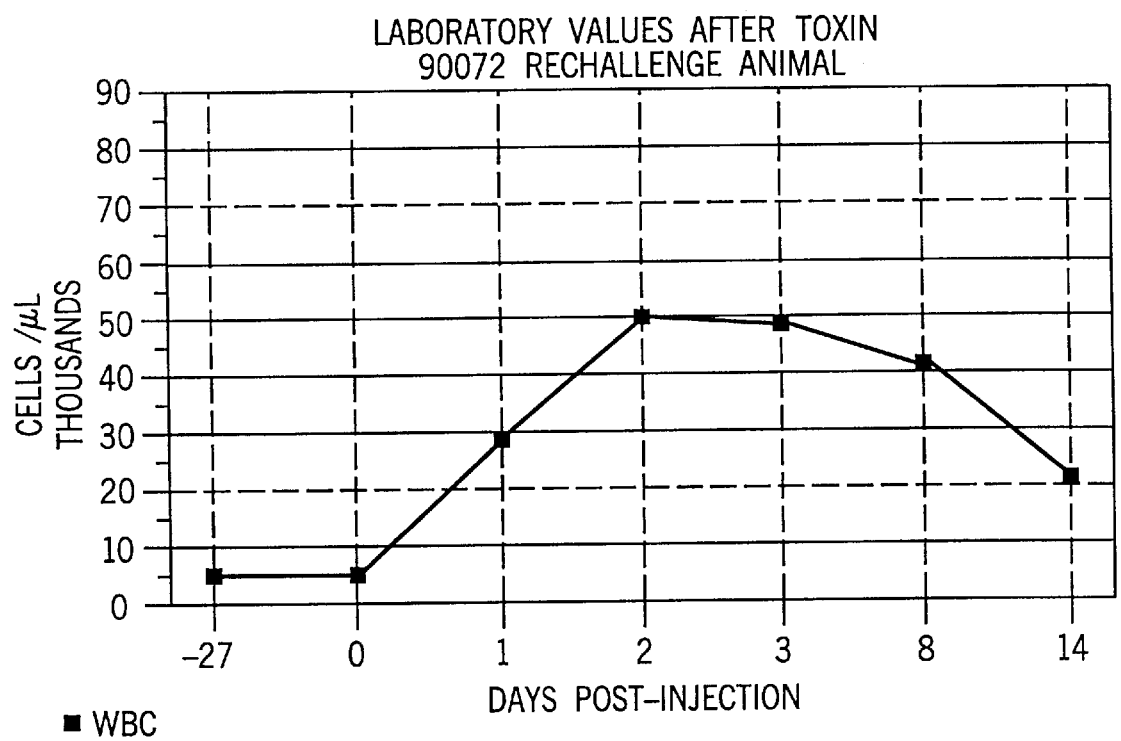

Leukocytosis in Treated, Infected Animals (intravenous challenge) PTx 100 μg

|  | PBMC req'd for positive | Corr. CD4 Number | tissue/blood virus load |
|---|---|---|---|
| 90054pre | 1,000 | 220 | |
| 8 d. | 5,000 | 670 | 5.9 |
| 21 d. | 1,000,000 | | |
| leukocytosis => 18X | | | |
| 90061pre | 10,000 | 3310 | |
| 8 d. | 1,000 | 177 | 80.4 |
| 21 d. | >1,000,000 | | |
| leukocytosis => 4.3 X | | | |
| 90072 pre | 50,000 | 18,000 | |
| 8 d. | 100,000 | 23,800 | 9.3 |
| 21 d. | >1,000,000 | | |
| leukocytosis => 7X | | | |

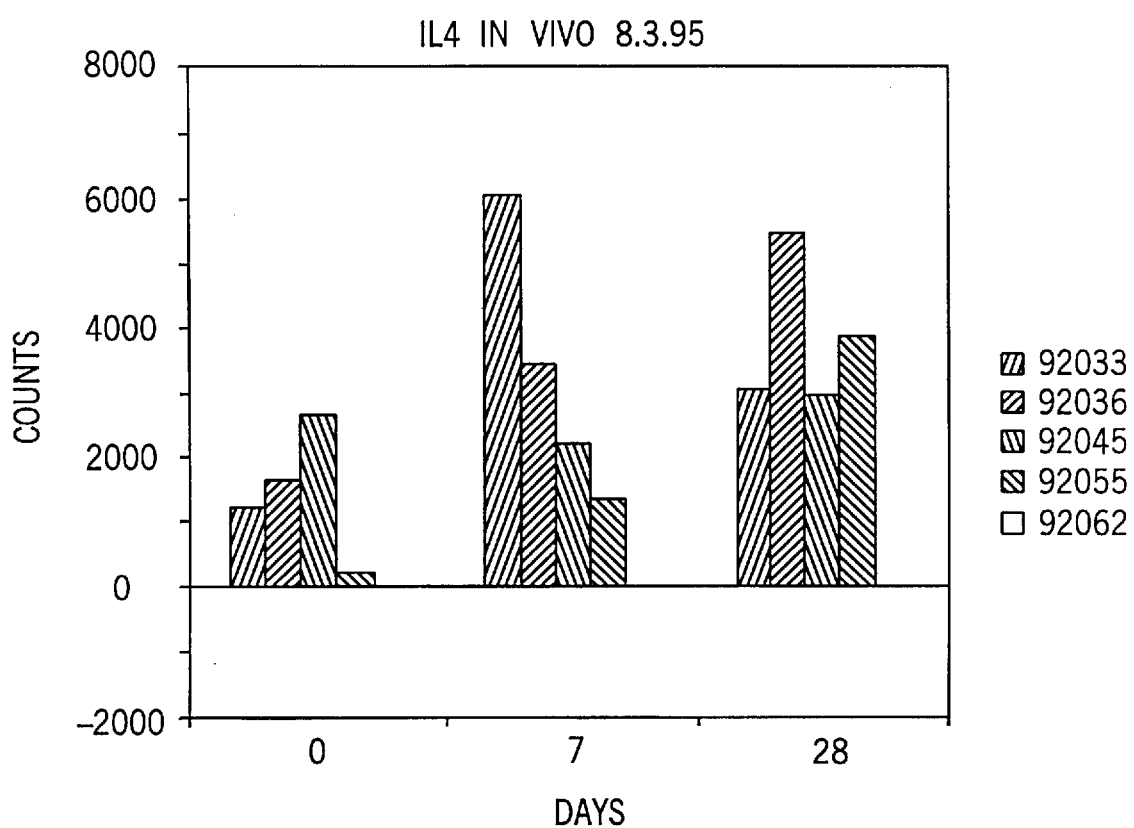

PERTUSSIS TOXIN INDUCED LYMPHOCYTOSIS

CROSS-REFERENCE TO RELATED APPLICATIONS

This application is a divisional of Ser. No. 08/793,655, filed Apr. 23, 1997, now U.S. Pat. No. 5,888,726, which in turn is the National Stage of PCT/US95/11004 filed Aug. 29, 1995, which in turn is a Continuation-In-Part application of Ser. No. 08/299,890, filed Sep. 1, 1994, now abandoned.

STATEMENT REGARDING FEDERALLY SPONSORED RESEARCH AND DEVELOPMENT

This invention was made with United States Government support awarded by the National Institute of Health (NIH), Grant Nos. R01 A124591, U01 A133237. The United States Government has certain rights in this invention.

BACKGROUND OF THE INVENTION

Acquired Immune Deficiency Syndrome, or AIDS, causes an immunosuppression of certain cells critical to eliciting an immune response. AIDS is caused by the Human Immunodeficiency Virus or HIV.

AIDS is characterized by progressive debilitation of the host immune system, chronic wasting disease, chronic diarrhea, dementia, and increased incidence of unusual cancers. A consequence of decreasing immune system function is the onset of life threatening opportunistic infections due to pathogens such as *Pneumocystis carinii* and *Mycobacterium avium* complex that are rarely serious for immunocompetent individuals. Wasting disease and chronic diarrhea are the principal enteropathic sequelae of HIV-1 infection. Dementia is believed a consequence of HIV-1 infection in the central nervous system. The unusual cancers include lymphoma of the brain and Kaposi's sarcoma that develops in almost one third of AIDS patients. The principal laboratory sign of progressive HIV-1 infection is the loss of CD4+T lymphocytes and this change is linked to the profound dysregulation of immune responses and the general immunodeficiency in the cell mediated branch of the immune system.

HIV is a retrovirus or RNA virus which has the ability to copy its RNA into new double stranded DNA that can be integrated into the DNA of an infected cell. This conversion from RNA to DNA is catalyzed by an RNA directed DNA polymerase or reverse transcriptase (RT). Retroviruses exist in a multitude of forms involving varying degrees of infectivity and pathogenicity. Endogenous retroviruses are distinguished from exogenous retroviruses in that they are usually carried benignly in the germ line. Most of these endogenous retroviruses are defective. Exogenous retroviruses are more pathogenic and fall in four major groups: (1) Murine Leukemia virus group; (2) the mouse mammary tumor virus/Rous Sarcoma virus group; (3) the human T Cell leukemia virus (HTLV) group; and (4) the lentivirus group. HIV falls into the last category.

Specifically, three outbreaks of primate lentiviruses have been recognized: HIV-1 in central Africa, Asia, North America and Europe; HIV-2 in West Africa; Simian Immunodeficiency Virus (SIV) in captive and wild nonhuman primate populations. Comparative analysis between HIV-1 and HIV-2 nucleotide sequences show little homology, only 42%. Conversely, HIV-2 is closely related to SIV.

HIV infection in humans and SIV infection in monkeys is primarily a disease involving viral replication within the individual lymph nodes and other solid tissues of the secondary immune system. An early consequence of infection is the onset of lymphadenopathy indicating the substantial involvement of tissues in the secondary lymphoid system (the solid tissue sites including linings of the mucosal surfaces, lymph nodes, spleen, thymus, and others). The period of clinical latency disguises an underlying virological activity as HIV-1 infection disseminates throughout the secondary lymphoid system and causes the progressive destruction of immune capacity.

The lymph node is a microcosm of HIV and SIV infection that highlights the competition between virus destruction and virus replication because both of these processes require T lymphocyte activation. T lymphocytes are included in the category of white blood cells and are produced in spleen, thymus, and bone marrow. They are essential elements in all immune reactions by virtue of their key regulatory functions. Another population of immune cells are termed macrophages; they are also involved in several immune functions and are considered essential. Specific subpopulations of T lymphocytes and macrophages present the CD4 molecule on their cell surface. This molecule binds HIV-1 to these cells and facilitates their destruction. The level of circulating T lymphocytes in AIDS patients is depressed and this is especially evident for the T helper cell subset. Whereas the ratio of $T_H$ to $T_S$ (T suppressor cells) cells in normal humans averages 2.3, the $T_H/T_S$ ratio in AIDS patients is less than 0.9.

Research on therapy for HIV-1 infection principally utilizes conventional approaches that identify specific biochemical features of this virus and develop small molecule drugs to block the cycle of virus replication. These methods have been largely unsuccessful because of the highly variable nature of this virus, leading to rapid evolution of drug resistant variants, the highly regulated nature of the virus life cycle, allowing extended periods of decreased virological activity without loss of viral genomic sequences, and the intimate relationship between factors that promote virus replication and those factors that promote immune responses to the virus.

Vaccine efforts have not been successful and practical difficulties in animal model development and human clinical testing combine to slow progress in this area.

Not only have vaccines failed in combating AIDS, but various drugs also do not rid the body of the virus. For example, Azidothymidine, or AZT, is a thymidine analogue which inhibits in vitro replication of HIV. Unfortunately, this drug does not work as well in an in vivo environment and has serious side effects.

Current efforts in therapy development include a variety of strategies for increasing immune system activity and/or decreasing CD4 cell killing. Therapeutic vaccination and adoptive transfer of CD8+T-lymphocyte clones are intended to increase effectiveness of immune responses to virus. Genetic modification of CD4+T-lymphocytes including transdominant modifications of HIV proteins, RNA decoys, antisense RNA, ribozymes and modifications of cellular proteins (intracellular antibodies, soluble CD4) are all intended to increase cellular resistance to virus killing mechanisms. Several of these strategies are now entering clinical trials.

However, significant conceptual and technical hurdles must be overcome before the promise of gene therapy or vaccines for HIV infection can be realized.

It is clear from the difficulty in treating HIV infection that it has a complex and varied disease course. Therefore, it is necessary to evaluate the relationship between route of infection, virus strain, and likely pattern of disease progression as important steps toward understanding the factors controlling epidemic HIV spread and the resulting diseases. Imprecise information about the route and timing of initial infection, the possibility that reinfection can occur, and the complex virus populations present within infected individuals are important confounding factors that inhibit understanding the host pathogen's interactions involved in epidemic infection.

SUMMARY OF INVENTION

The current invention establishes a new approach to therapeutic intervention in the cycle of HIV-1 infection and progressive disease. Distinct from conventional approaches that are directed at specific aspects of viral biochemistry, the current invention utilizes fundamental insights into the pattern of virus replication and dissemination. These were derived from human and nonhuman model studies, to interrupt the cycle of infection and to promote reacquisition of key immune responses in already infected individuals. The descriptive term "Therapeutic Remodeling" embodies the fundamental aspect of this discovery. As the viral infected immune system is not capable of mounting a protective response or of eliminating the virus, we disrupt the condition, eliminate sites of active virus replication, promote reacquisition of immune response capacity, and engender a positive therapeutic response. It involves eliciting lymphocytosis in order to reveal the sequestered HIV or SIV in the lymph tissues to make possible an accurate determination of total virus load for HIV (or SIV) and to engender a situation consistent with therapeutic drug effects. The lymphocytosis itself causes an alleviation of the AIDS symptoms and a reduction in the viral load.

It has been found that the administration of pertussis toxin (PTx) in an amount of between 1 μg/kg to about 50 μg/kg induces lymphocytosis and alters the activity of secondary lymphoid tissue. Central to this approach is the question of whether the lymph nodes and lymphocytes are important to fight disease or whether in the case of AIDS they act as a substrate for the immunodeficiency virus.

Lymphocytosis is a condition wherein the normal trafficking of lymphocytes from blood into the solid lymphoid tissue sites is inhibited; upon normal rates of lymphocyte entry from tissue to blood and under the condition where the return pathway is blocked, lymphocytes accumulate for a specified interval in the peripheral blood stream. This release interrupts the cycle of viral replication and constitutes one part of the therapeutic benefit. The inventor's approach to development of a therapeutic agent for treatment of AIDS is based on the basic nature of viral pathogenesis in the disease. HIV infection in humans and SIV infection of monkeys, is primarily a disease involving virus replication within the individual lymph nodes and other solid tissues of the secondary immune system. Therefore, the effort is directed at altering the distribution and activity of these cells in the immune system. By releasing lymphocytes from solid tissue sites, such that they reside temporarily in the peripheral blood, lymphocytosis also causes varied effects including a massive increase in white blood cell count and increase in the amount of viral infected cells in the blood (but without plasma viremia). In addition, the lymph nodes had reduced virus levels during the interval after PTx treatment.

In addition to the aforementioned effects of PTx, this molecule also causes cytokine synthesis. Cytokines are released by many types of immune cells and act as intercellular mediators by stimulating other immune cells thereby generating an extremely rapid immune response to a specific antigen. Lymphokines, tumor necrosis factor (TNF), IL-1α, IL-4, IL-6, IL-10 and interferon gamma are all examples of cytokines. It has been found that PTx induces production of TNF and interferon gamma in vitro. TNF is released by leukocytes and macrophages in response to bacterial infection and other challenges to a living system. Interferon gamma is important in exerting antiviral activity. Both TNF and interferon gamma have effects in combating HIV and SIV.

It is an object of this invention to allow a detailed analysis of the total virus burden in the infected animal or human which is not possible by any other current approach. Presently, viral burden is measured via extrapolating data based on values obtained from standard blood samples. This method has proven to be quite inaccurate.

A second object of this invention would be to stimulate cellular and humoral immunity mechanisms in the infected animal or human with the consequence of increasing the protective host response to the virus.

A third object of this invention is to provide a treatment for HIV infection and/or AIDS related symptoms. This HIV or AIDS treatment may be used by the administration of pertussis toxin itself or as a preconditioner in conjunction with other treatments.

The fourth object of this invention is to evaluate the efficacy of drug treatments or vaccines that are designed to either completely prevent HIV infection or to clear the virus from an infected individual.

The fifth object of this invention is to more accurately study the effects of HIV infection on the body CD4+cell levels during the course of the infection and/or disease.

Another object is to use an immunomodulatory therapy to combat persistent virus infections via increased immune responses and regulated expression of cytokine expression.

Still another object of this invention is to elicit an immunomodulatory effect upon a system in order to combat HIV or SIV infection.

BRIEF DESCRIPTION OF THE DRAWINGS

FIG. 1 is a table of data obtained over time from the blood of three uninfected rhesus monkeys after being injected with 25 μg, 50 μg and 100 μg of pertussis toxin respectively.

FIGS. 2A–2D are tables of data obtained over time from the blood of an uninfected rhesus monkey injected with saline as a control (FIG. 2A), and of three uninfected rhesus monkeys after each were injected with 100 μg of pertussis toxin. (FIGS. 2B–2D).

FIG. 3 is a graph illustrating leukocytosis for uninfected animals after being injected with 100 μg of pertussis toxin.

FIGS. 4A–4B are tables of data obtained over time from the blood of two SIV infected rhesus monkeys after each were injected with 100 μg of pertussis toxin.

FIG. 5 is a graph illustrating leukocytosis for SIV infected animals after being injected with 100 μg of pertussis toxin.

FIG. 6 is a graph illustrating an HIV-2 ELISA Assay used to determine serum IgG antibody specific for SIVmac titers at various monthly intervals after injection of 100 μg pertussis toxin.

FIGS. 7A–7C are tables of data, and FIGS. 7D–7F illustrate corresponding graphs of WBC data, obtained over time from the blood of three SIVmac infected rhesus monkeys after each were injected with 100 μg of pertussis toxin.

FIG. 8 is a graph illustrating leukocytosis for the infected animals of Example 6.

FIG. 10 is a graph illustrating IL-4 expression after pertussis toxin administration to SIV infected rhesus macaques over time.

DETAILED DESCRIPTION OF THE PREFERRED EMBODIMENT

Figure 2C:

Pertussis (PTx) is derived from *Bordetella pertussis* (whooping cough bacterium). PTx is a hexamer of 5 dissimilar subunits, combined molecular weight is approximately 117,000 Daltons. PTx is in the class of "A-B toxins", which includes cholera and diphtheria toxins. PTx consists of two functionally distinct components, one binds to the cell membrane, the other enters the cell where it exhibits its enzymatic actions.

Disassociation of the PT toxin will give two active moieties, the $S_1$, protein, also called the A (active) protomer and the remaining pentamer, called the B (binding) oligomer. The B oligomer moiety serves to bind to the cell membrane surface glycoproteins via the D1 and D2 dimers. There is then a slow internalization of the A-molecule.

The B-oligomer is a potent T-cell mitogen stimulating lymphocyte transformation. This mitogenic activity requires "divalent" binding of both the D1 and D2 dimers.

The A-molecule, after cellular internalization, undergoes intracellular processing to the active ADP-ribosyltransferase form. The activated A-protomer then targets specific GTP-binding proteins (G-proteins); these G-proteins act as message transducers—most importantly in the cAMP pathways.

Chemically inactivated pertussis toxin is currently being tested as an acellular intramuscular vaccine for pertussis or whooping cough. For the vaccine effect, 5–10 micrograms of the toxin are injected. In order to induce lymphocytosis in rhesus monkeys, a 100 micrograms of the toxin are injected intravenously.

Many compounds list lymphocytosis as a side effect, but the effect is minimal, i.e. 40–60 percent effect. In the present therapy, one desires a minimum of 300% effect. Specifically, one wants to release at least 300% of the total lymphocytes into the blood so that there is no local reservoir left where the viral infected lymphocytes can "hide". This is an important result because studies of HIV infection in man generally conclude that total virus load exceeds blood virus load by a factor of 10 or more.

This induction of lymphocytosis appears to be therapeutic in and of itself. In addition, the pertussis toxin injection could be used as a pre-conditioner. As a pre-conditioner, PTx could be combined with leukapheresis (a method to remove lymphocytes from the blood) or used as an adjuvant to other aggressive antiviral therapeutic approaches. For example, an HIV protease inhibitor or treatment using recombinant DNA technology could be administered subsequent to the PTx treatment. In the case of leukapheresis, the apparent action of the pertussis toxin to induce bone marrow regenerative activity would help rapidly reconstruct the immune system once the infected cell population is removed.

The induced lymphocytosis of viral infected and uninfected cells makes them available for ex vivo manipulations that may be too toxic for in vivo administration and could include delivery of antiviral gene constructs, enzymatically active nucleic acids, inhibitory oligonucleotides, and synthetic or naturally occurring compounds that block the action of specific viral proteins. This invention also allows use of modified oligonucleotides and ultraviolet light to inactivate viral genomes and other approaches that are practical for in vitro application which, until now, could not be applied to the situation of infected cells in the living person.

Experimental data provided here establishes the value and practical application of PTx as a compound for inducing lymphocytosis in primates, with the attending implications of therapeutic benefit and facilitation of adjunct therapies. The essential feature of this invention is the conceptual development of therapeutic remodeling as an approach to AIDS therapy. Toxin molecules similar to PTx and other distinct immunomodulatory compounds may have similar effects and could prove valuable as agents for inducing therapeutic remodeling.

The primary immunomodulatory effect of PTx is cytokine production. Since cytokines have a negative effect on the replication of various pathogenic agents including bacterial, fungal and viral infections, the effect of PTx stimulated cytoline production would be extremely beneficial in combating such infections as HIV or SIV.

Due to the fact that SIV and HIV are both lentiviruses with the same pathogenic effects, characteristics, and evolved from a common source, it is logical that lymphocytosis would have the same effect on SIV-infected primates as HIV-infected humans. Sharp, P M, Li W-H: "Understanding the Origin of AIDS Viruses", Nature 1988; 336:315.

METHODS

Example 1

Administered 25 μg, 50 μg, and 100 μg PTx to rhesus by i.v. injection. One year old rhesus monkeys were selected at random from the Wisconsin Regional Primate Research Center colony. They were determined to be negative for Type D retroviruses and for SIV by serological testing and by in vitro virus isolation assays. The SIV-negative diagnosis was confirmed by polymerase chain reaction assays for SIV long terminal repeat sequences.

Sterile, lyophilized pertussis toxin (List Biological Laboratories, Inc., Campbell Calif.) was aseptically reconstituted with sterile water for injection (Abbott Laboratories, North Chicago Ill.) to concentration of 100 μg/ml. Toxin was injected into the saphenous vein of each male uninfected rhesus monkey at rate of approximately 1 cc/min. Site of injection was observed for negative reactions before returning animals to their cages.

Blood was drawn in vacutainer (Becton-Dickenson) blood tubes and submitted to commercial clinical laboratory (General Medical Laboratories, Madison, Wis.) for Complete Blood Counts (CBC) and Chemistry Profiles (Vet-20). Collected blood samples at regular intervals ( day 0, day 3, day 7 etc.) for CBC.

Results: There was a dramatic increase by day 7 for animal 90144 that received $^{100}$ μg PTx. Lower doses showed no significant increases; later time points for low dose group was collected but observed no significant deviations from normal. At 25 μg and 50μg PTx an increase in the % lym was observed but this was not accompanied by the dramatic increase in WBC. This could be considered a mild lymphocytosis but not a leukocytosis (increase in all white blood cell populations). No adverse reactions were seen. See FIG. 1.

Conclusion: Use at least 100 μg dose per animal to induce lymphocytosis. Specifically, between 20 μg/kg and 50 μg/kg is sufficient.

Example 2

The first uninfected animal (male) on this chart (87012) was injected with saline as a control. The other three uninfected animals (1 male, 2 females) were injected with 100 μg PTx as outlined in Example 1. Blood samples collected as outlined in Example 1 at regular intervals (day 0, day 1, day 2, day 4, day 8, etc.). Leukocytosis was evaluated by CBC and collected clinical chemistries (Vet 20 panel that included blood electrolytes, enzymes and other protein levels, glucose, etc.).

Standard flow cytometric analysis of lymphocyte subpopulations (CD4, CD8 and CD20) was also performed.

Results: The column marked % inc (percentage increase of the WBC count over baseline) is an indication of leukocytosis. For example, the 842% increase for 87031 on day 7 would be listed as an 8.42 times increase as the peak value.

Figure 3:
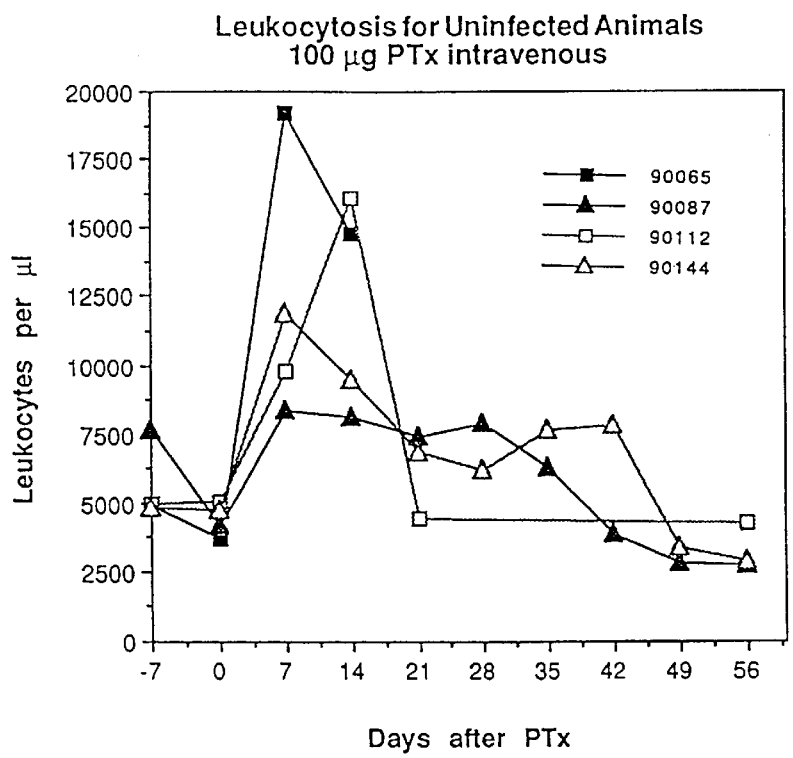

No changes in the patterns specific to sex or age have been noted. Significant lymphocytosis and leukocytosis was noted in all animals with a range of WBC increase from 2.4 times to 12.5 times. Normally blood contains between 5% and 12% of the total white cell count in the body and this population exchanges with the cells in solid tissues. A leukocytosis of 20 times would certainly place all tissue associated cells into the blood. A leukocytosis of 12 times would be complete if we assume the higher value of 10% cells normally in the blood. The pattern of leukocytosis was nearly identical in all cases and WBC counts peaked around day 7 to 14 and returned to normal by day 22 after PTx injection. See FIGS. 2A–2D. FIG. 3 illustrates the same result but with a different group of uninfected monkeys.

Conclusion: 100 μg PTx dose routinely induces leukocytosis and lymphocytosis. Relative changes in the percentage of lymphocytes are not reliable and only absolute numerical increases are relevant. The appearance of mature lymphocytes in the peripheral blood following PTx treatment is consistent only with release of cells from the secondary lymphoid tissues and is not the consequence of generating new cells from bone marrow. Some evidence exists for bone marrow activation (primarily the percentage of segmented and banded cells which are early products of new cell division in the bone marrow) though this is clearly not the source of increased lymphocytes in circulation.

Example 3

Two rhesus monkeys in this panel were inoculated with 100 μg PTx (as outlined in Example 1) three years after infection with SIVmac (simian immunodeficiency virus of macaques) given by intrarectal inoculation. Viral inocula were prepared in 1 ml of RPM 11640 medium without serum supplement. Intrarectal inoculation was performed by inserting a Fr. 18 soft pediatric nasogastric catheter approximately 10 cm into the rectum. The virus inoculum was delivered in 1 ml and the catheter was flushed with an additional 5 ml of medium.

The SIVmac$_{251}$ virus stock was obtained from Dr. Ronald C. Desrosiers (Harvard University and New England Regional Primate Research Center) and was amplified by several passages on rhesus PBMC with a final passage in CEMx174 cells. Virus doses from 0.1 to 1,000 infectious doses (ID) were used.

To confirm animals are SIV positive after SIV exposure, infection evaluations were performed by assaying virus-specific reverse transcriptase present in the culture fluids, using a standard assay kit (Boehringer-Mannhein). The Boehringer-Mannhein (Indianapolis, Ind.) non-radioactive ELISA kit (product #1468-120) was utilized. Specimens were prepared by spinning 2.4 ml of culture supernatant in a Beckman microfuge at 12000x for 15 minutes (removes cellular debris) followed by ultracentrifugation in a Beckman L8-M centrifuge, using SW60 rotor for 35,000 rpm for 33 minutes to pellet the virus particles. Viral pellets were frozen at −80° C. prior to use. Viral pellets were dissolved in 40 μl of lysis buffer then incubated with template/primer hybrid and digoxigeninlabeled and biotin-labeled nucleotides. The resulting DNA has biotin and digoxigenin groups attached, the biotin binds to a streptavidin bound plate surface and the digoxigenin is bound by an antidigoxigenin, linked to peroxidase. The complexes are washed and reacted with substrate to give a colored product. Values greater than or equal to 10 μg/well were scored positive for virus production.

Hematologic data was collected and analyzed as outlined in Example 1.

Results: FIGS. 4A–4B list hematologic data for the two PTx treated animals wherein the date refers to days after treatment with negative values showing pretreatment points. These data include absolute cell counts but are otherwise the same as for previous data.

Example 4

Virus isolation and viral DNA load determination was evaluated in the animals of Example 3. Virus isolation was performed on isolated PBMC approximately 7 months after the PTx treatment. Specifically, 4–7 ml of whole, heparinized blood was carefully layered over 5 ml of ficoll solution (Histopaque 1077, Sigma Chemical Company, St. Louis Mo.). Ficoll tubes were spun in refrigerated centrifuge (Beckman TJ-6) at 800 g for 30 minutes. Plasma was carefully drawn off and the cells at the interface washed with phosphate buffered saline (PBS). After PBS wash the cells were resuspended and treated with 2 ml of ACK buffer to remove unwanted red blood cells. After ACK treatment the cells were washed again in pBS and resuspended in RPMI-1640 media (GibcoBRL, Grand Island N.Y.) with 10% fetal bovine serum (GibcoBRL). The peripheral blood mononuclear cells (PBMC) were counted with an improved Neubauer Hemocytometer, using standard technique. Suspensions of PBMC were made at 2×10$^6$ cells/ml in RPMI-1640/10% FBS. Six-well microtiter plates (Corning Glass Works, Corning N.Y.) had 500 μl of media added to well #1 then 900 μl to subsequent wells; 500 μl of the PBMC suspension was added to Well #1, then 100 μl serial dilutions were done in subsequent wells (10$^6$, 10$^5$, 10$^4$, 10$^3$, 10$^2$, and 10$^1$ cells/well). 2×10$^5$ CEMx174 cells were added and total volume adjusted to 2.5 ml with RPMI-1640/10% FBS. Plates were examined every 3–4 days and scored for viral cytopathic effects (CPE).

Standard flow cytometric analysis of lymphocyte subpopulations was also performed.

Figure 5:
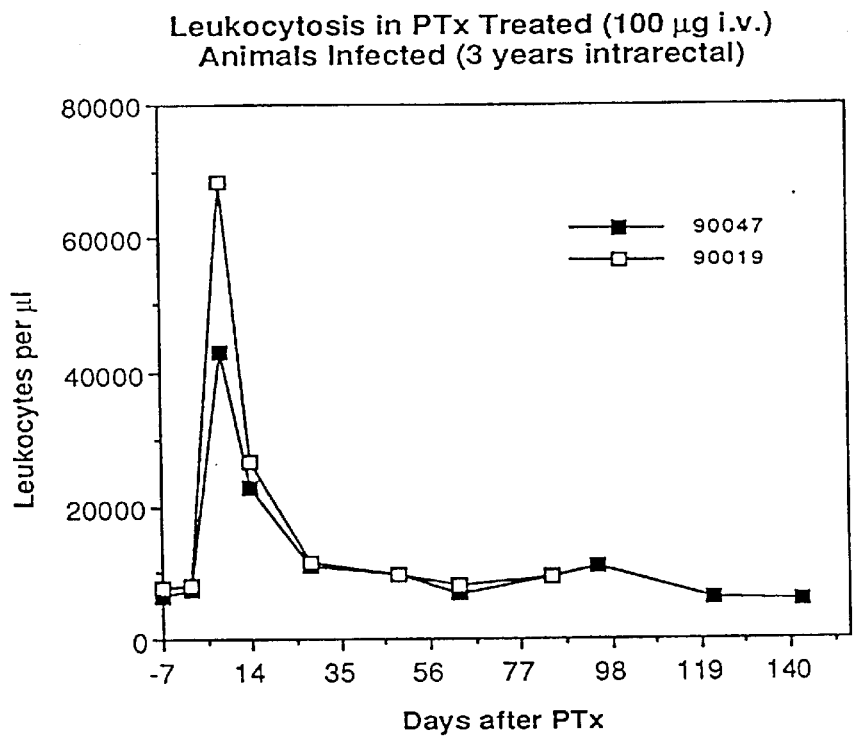

Results: FIG. 5 Illustrates the measure of virus load following PTx induction. The frequency of infectious cells is inversely proportional to the number of cells required to generate a positive virus detection. The assay examines the ability of a standard cell line to capture small amounts of virus released from infected peripheral blood cells and is a sensitive measure of infection frequency. For animal 90019, the number of PBMC (peripheral blood mononuclear cells) required for a positive virus isolation was 10,000 prior to PTx treatment. From standard flow cytometric analysis of lymphocyte subpopulations, we know that 25% of these cells are CD4+T lymphocytes, the fraction that is infected with SrV. Therefore, the minimum number of CD4+T cells required for positive virus isolation is 2,500. By 8 days after PTx treatment, the WBC count was elevated by 10 fold (leukocytosis=10X). At this time, the number of PBMC for a positive virus isolation was 1,000 and the corrected CD4+T cell count was 250 cells minimally required for positive virus isolation. Based on these values, we calculate the ratio between virus load present in blood prior to PTx treatment and virus load present in blood after PTx treatment. The calculation is: (minimum CD4+number before÷minimum CD4+number after)×leukocytosis factor. In the example cited here: (2500 CD4 before÷250 CD4 after)×10 leukocytosis factor=100 fold difference.

Conclusions: At a minimum, the total virus load in animal 90019 at 3 years after intrarectal infection with SIVmac, exceeded the virus load apparent in PBMC by a factor of 100. Alternatively, peripheral blood in animal 90019 contained normally only 1% of total virus in the body.

FIG. 5 continues with similar data for animal 90047. In this case, we had two different data points for virus isolation after PTx treatment. Using the more conservative figures the calculation becomes: (8000 min. CD4 before÷20 min. CD4 after)×9 leukocytosis factor=3,600 fold difference between virus load present in blood and total virus load in the body.

FIG. 5 includes crucial information about therapeutic benefit of PTx treatment. Note that the number of PBMC required for positive virus isolation increases dramatically in the time following peak leukocytosis. The data points marked >1,000,000 indicate values that were negative in our assay meaning we were unable to isolate virus. The time intervals listed show that negative or greatly reduced virus loads were a feature of both animals 90019 and 90047 following PTx treatment. These results indicate that PTx induced leukocytosis has therapeutic benefit during stages when the virus is mostly associated with lymphoid tissues, i.e. when the immune system is relatively intact. This will help define the targets for clinical intervention with this drug.

Example 5

HIV-2 ELISA Assay was used to determine serum IgG antibody specific for SIV mac titers in the animals of Example 3 (and Example 4) at various monthly intervals after PTx 100 μg treatment. The PTx treatment and blood collection was done in accordance with Examples 3.

The Genetic Systems Corporation (Seattle WA) ELISA kit (Product #0220) was utilized to determine antibody levels. The HIV-2 and SIV antigens are so close immunologically that the antibodies are cross-reactive. Serial dilutions of plasma were assayed to establish the titer of reactive antibodies. The kit utilizes inactivated HIV-2ROD virions bound to a microtiter plate; the plasma antibodies bind to the antigen and detection is by peroxidase labeled goat anti-human immunoglobulin. Cut-off levels were established using positive control samples.

Figure 6:
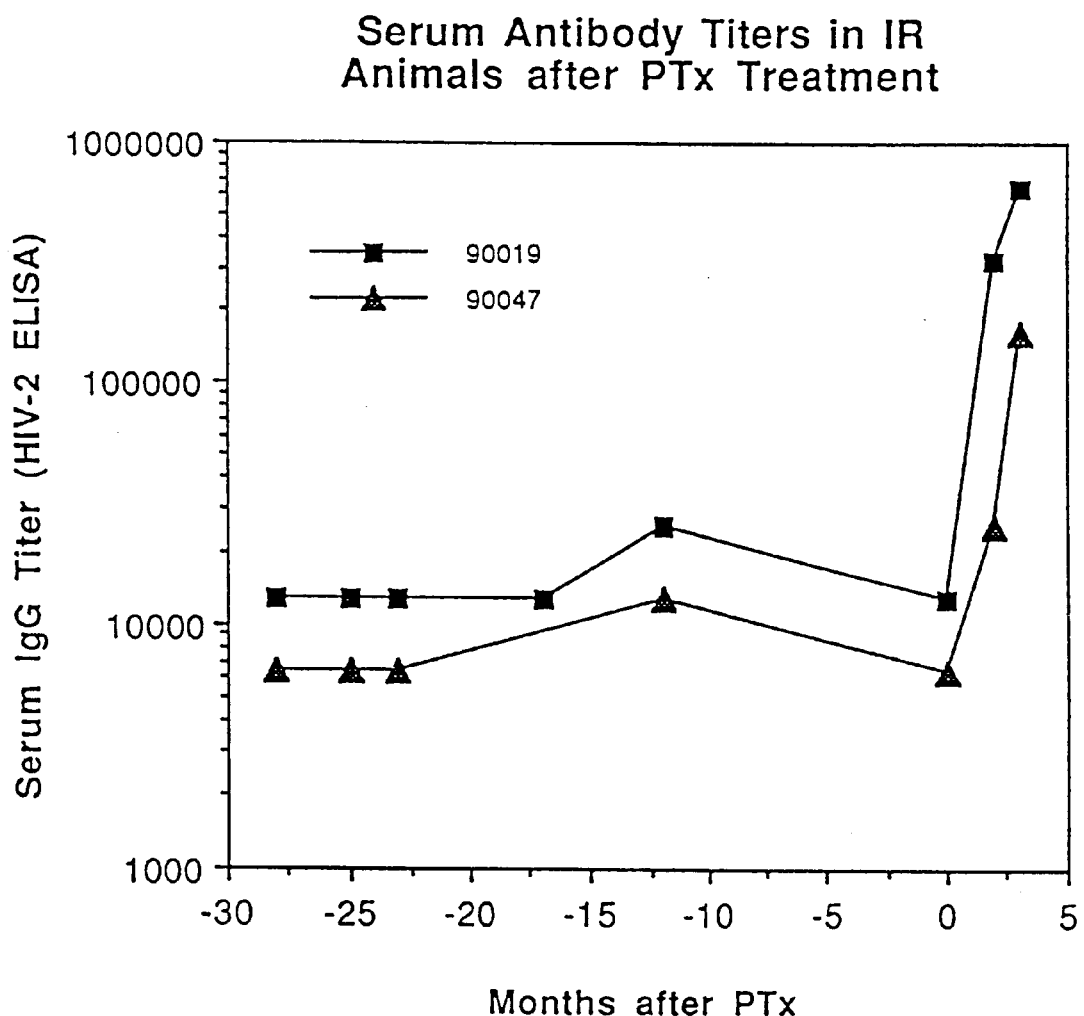

Results: FIG. 6 shows our preliminary work on mechanisms for virus clearance following PTx treatment. Here, we show that serum antibodies specific for SIVmac increase dramatically following PTx treatment. The increase are astonishing considering the 30 months of stable antibody levels that preceded PTx treatment.

Example 6

Three rhesus monkeys in this panel were inoculated with 100 μg PTx (as outlined in Example 1) three years after infection with SIVmac as outlined in Example 3. This exposure created an unusual infection condition we term indolent infection. Thirty months after this exposure, they were given a second dose of SIVmac by intravenous injection whereupon they developed acute and progressive infection. Infection status was determined by the method described in Example 3. Four months after the second virus exposure, these animals were treated with 100 μg PTx as described in Example 1.

Hematologic data was collected and analyzed as outlined in Example 1.

Figure 7D:
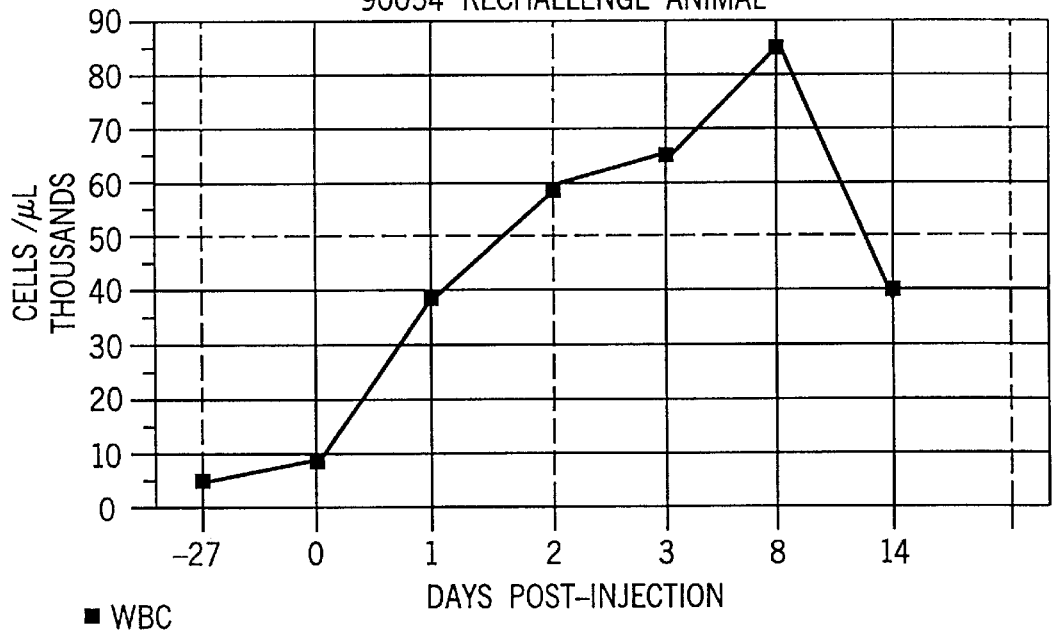
Figure 7E:
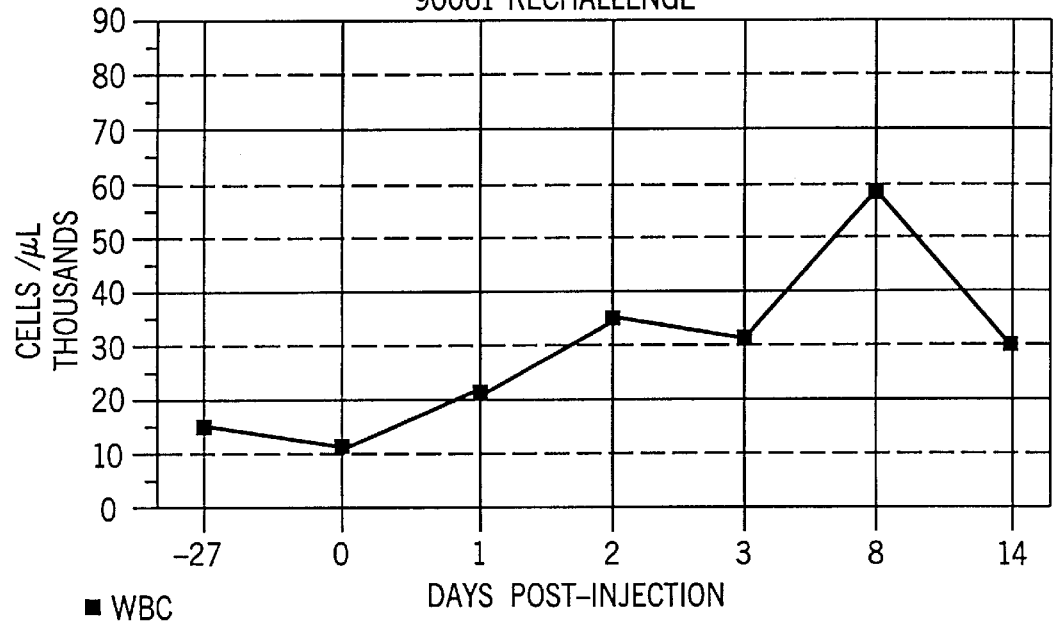

Results: FIGS. 7A–7C list the hematologic data.

Example 7

Virus isolation and viral DNA load determination was evaluated in the animals of Example 6. Virus isolation was performed on isolated PBMC in the same method as Example 4.

Results: See FIG. 8. The differences are smaller in these cases (5.9 fold, 80.4 fold, and 9.3 fold). This is not a surprising difference. We know that intravenous infection is much more aggressive than intrarectal infection and tends to be more widely distributed, with greater destruction of lymphoid tissues, and a correspondingly lower ability to retain infected cells. Additionally, these animals are probably farther along in the pathway of disease progression than the intrarectally infected animals, despite the large differences in time scale. Intrarectally infected animals progress much more slowly to disease (at least 3 years before clinical signs and a much longer but undefined interval to death). Among intravenously infected animals, 40% of a group is expected to succumb to clinical disease by 4 months after inoculation. The group used here was four months after inoculation.

Figure 8:
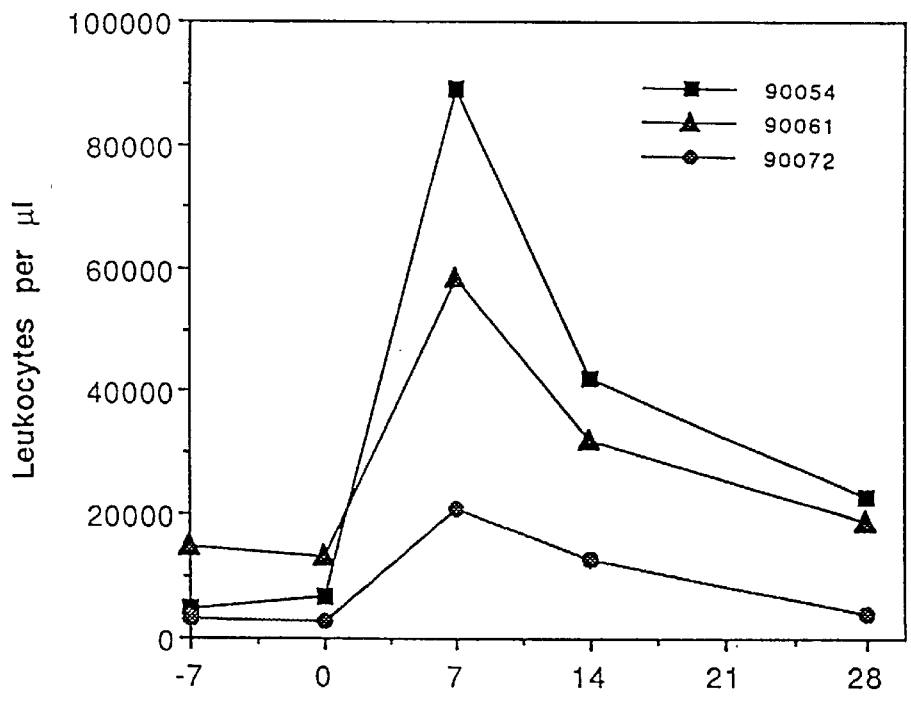

FIG. 8 (like FIG. 5) also includes crucial information about therapeutic benefit of PTx treatment. Again the number of PBMC required for positive virus isolation increases dramatically in the time following peak leukocytosis. The data points marked >1,000,000 indicate values that were negative in our assay meaning we were unable to isolate virus. This was observed for animals 90054, 90061, and 90072 with the caveat that decreases in virus isolation were less dramatic and were of shorter duration. Again these results to indicate that PTx induced leukocytosis has therapeutic benefit during stages when the virus is mostly associated with lymphoid tissues, i.e. when the immune system is relatively intact.

Note: All the infected animals showed great improvement after PTx administration. The SIV infected animals had shown a complete remission of the SIV disease and its symptoms after PTx injection. They had gained weight, their behavior had changed to the normal aggressive behavior, and their previously arrested sexual development had changed to sexual maturation within 30 days of the treatment. All PTx treated infected animals are in obviously better health than before the treatment and none have died despite the dramatic elevations in blood virus load.

Example 8

This example illustrates that CD8+T cells in blood are increased after therapeutic dosing of SIV-infected rhesus macaques.

Administration of pertussis toxin (25 μg/kg) to SIV-infected rhesus macaques provided a statistically significant increase in survival. The experiment was analyzed at 300 days after SIV infection. Using Kaplan Meier analysis and log rank testing, the increased survival in treated animals compared to untreated animals was significant at the p alpha=0.05 level.

Figure 9:
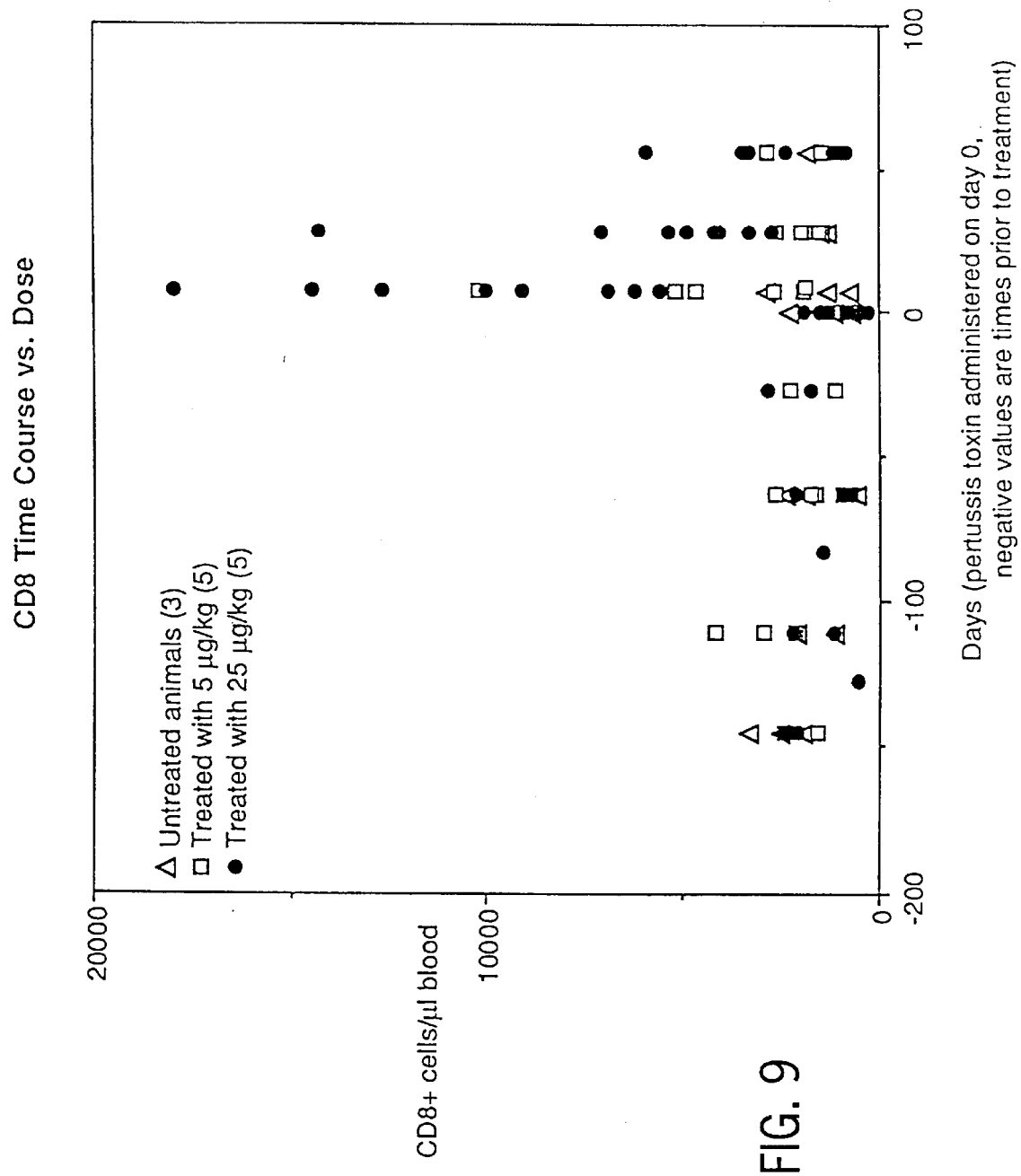
FIG. 9 is a graph illustrating different CD8+T cell levels in blood of untreated and PTx treated SIV infected rhesus macaques over time.

Increased survival was highly correlated with sustained increases in peripheral blood CD8+T cells. Using Student's t test for pairwise comparison, the differences in circulating CD8+T cells between untreated and treated (25 μg/kg), SIV-infected rhesus macaques was p<0.03. Thus, a high degree of correlation exists between elevated CD8+T cells in blood during the month after pertussis toxin administration and increased survival. Please see accompanying FIG. 9 showing data for increased CD8+T cells after pertussis toxin administration. The data were obtained with standard flow cytometry methods. A monoclonal antibody specific for CD8 on the cell surface was used to stain paraformaldehyde-fixed cells from rhesus macaques. The bound antibody was detected with a second fluorescently-labeled reagent specific for the probe antibody. The samples were passed through a flow cytometer and analyzed for fluorescence in coincidence with objects of the size and shape for intact cells. Data are reported as the absolute count of lymphocytes per μl blood that stained positively for the CD8-specific antibody (after appropriate controls and data corrections). Therefore, pertussis toxin increases the level of CD8+cytotoxic T cells in SIV infected rhesus macaques.

Example 9

This example illustrates that cytokine gene expression increases substantially after pertussis toxin treatment.

Cytokine gene expression was measured on the basis of mRNA accumulation in peripheral blood mononuclear cells. Total cellular RNA is prepared from PBMC or disaggregated tissues specimens. RNA samples are evaluated by agarose gel electrophoresis for integrity and content is measured by absorbance at 260 nm. 1 μg of total RNA is admixed with oligo dT and random hexamer to prime cDNA synthesis by AMV reverse transcriptase in the presence of RNasin. Individual cytokine gene sequences are amplified from this cDNA template using specific primers and standard PCR amplification protocols. Amplification products are separated by agarose electrophoresis and sequences are detected by Southern blot hybridization. The autoradiograms are analyzed by scanning densitometry and data are combined for triplicate samples. Data are reported here as the average of triplicate, base-line corrected densitometric values for each assay point with the mean value representing combined data for five SIV-infected rhesus macaques at 7 or 28 days after pertussis toxin treatment (25 μg/kg). Data were analyzed using the Tukey Kramer pairwise analysis with a required significance of p alpha 0.05.

IL-4 expression after pertussis toxin administration:

| Day | Mean Value | Standard Deviation |
|---|---|---|
| 0 | 1,350 | 1,011 |
| 7 | 3,463 | 1,932 |
| 28 | 4,150 | 1,109 |

Statistically significant differences between day 0 and day 7; and also between day 0 and 28. The raw data is included in graphical form as FIG. 10.

In reviewing the numerical data, this cytokine change was statistically significant at the p alpha 0.05 level. The specific regulation of IL-4 indicates that pertussis toxin has a direct effect on antibody production as this cytoline is regulatory for the humoral arm of the immune system.

In summary, the data argue for the unique nature of pertussis toxin as an immunoregulatory agent. Here, we show that pertussis toxin affects both aspects of the antiviral immune response, i.e. both cellular and humoral immunity mechanisms in AIDS, and this may account for its unique ability to increase survival.

What is claimed is:

1. A method for treating viral infections in mammals infected with a human immunodeficiency virus (HIV) or simian immunodeficiency virus (SIV) comprising:

administering to said individual an effective amount of pertussis toxin (PTx) wherein said effective amount is sufficient to cause lymphocytosis.

2. The method of claim 1, wherein said mammal is a human.

3. The method of claim 1, wherein said mammal is a primate.

4. The method of claim 1, wherein said administration Is via inoculation.

5. The method of claim 3, wherein said effective amount is between 1 μg/kg and 50 μg/kg of pertussis toxin (PTx).

6. The method of claim 1, wherein said pertussis toxin (PTx) is combined with an adjuvant.

7. The method of claim 1, further including the step of administering a subsequent HIV or SIV treatment to reduce or eliminate the pathogenic viral effect after administering said effective amount of pertussis toxin (PTx).

8. The method of claim 7, wherein said subsequent treatment is an antiviral treatment.

9. The method of claim 7, wherein said subsequent treatment is leukophoresis.

10. The method of claim 7, wherein said subsequent treatment is an HIV protease inhibitor treatment is administered.

11. A method for treating human immunodeficiency virus infection and acquired immune deficiency syndrome which comprises administering to a patient having said infection or syndrome an effective amount of pertussis toxin (PTx) wherein said effective amount is sufficient to cause lymphocytosis.

12. The method of claim 11 wherein said effective amount comprises about 1 μg/kg to about 50 μg/kg of pertussis toxin.

* * * * *

UNITED STATES PATENT AND TRADEMARK OFFICE
CERTIFICATE OF CORRECTION

PATENT NO : 6,027,731
DATED : February 22, 2000
INVENTOR(S) : C. David Pauza

It is certified that error appears in the above-identified patent and that said Letters Patent are hereby corrected as shown below:

Claim 5, col. 12, line 28　　　　Delete the word "Is" and substitute therefor
(original claim 26, line 2):　　　---is---

Signed and Sealed this

First Day of May, 2001

NICHOLAS P. GODICI

Attest:

Attesting Officer　　　Acting Director of the United States Patent and Trademark Office